US012605534B2

(12) United States Patent
Nalawade et al.

(10) Patent No.: US 12,605,534 B2
(45) Date of Patent: Apr. 21, 2026

(54) MEDICAL DISINFECTION DEVICE WITH VISIBLE DISINFECTION INDICATOR

(71) Applicant: Becton, Dickinson and Company, Franklin Lakes, NJ (US)

(72) Inventors: Praveen Nalawade, Belgaum (IN); Amit Kumar, Bengaluru (IN); Amruta Vaghela, Pune (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 647 days.

(21) Appl. No.: 18/071,869

(22) Filed: Nov. 30, 2022

(65) Prior Publication Data

US 2024/0173538 A1     May 30, 2024

(51) Int. Cl.
*A61M 39/16* (2006.01)
*A61L 2/18* (2006.01)
*A61M 39/20* (2006.01)

(52) U.S. Cl.
CPC .............. *A61M 39/20* (2013.01); *A61L 2/18* (2013.01); *A61M 39/162* (2013.01); *A61M 39/165* (2013.01)

(58) Field of Classification Search
None
See application file for complete search history.

(56) References Cited

U.S. PATENT DOCUMENTS

| | | | |
|---|---|---|---|
| 7,569,185 B2 | 8/2009 | Fischer | |
| 7,931,877 B2 | 4/2011 | Steffens et al. | |
| 9,192,449 B2 | 11/2015 | Kerr et al. | |
| 2008/0021381 A1 | 1/2008 | Lurvey et al. | |
| 2017/0341846 A1* | 11/2017 | Trznadel | A45D 34/042 |
| 2020/0276346 A1 | 9/2020 | Drmanovic | |
| 2021/0138223 A1 | 5/2021 | Jiang et al. | |

OTHER PUBLICATIONS

"PCT International Search Report and Written Opinion in PCT/US2023/081554 dated Apr. 2, 2024, 12 pages".

* cited by examiner

*Primary Examiner* — Elizabeth A Robinson
*Assistant Examiner* — Changru Chen
(74) *Attorney, Agent, or Firm* — Servilla Whitney LLC

(57) ABSTRACT

A disinfection cap or device for disinfecting medical connectors. The cap includes a visual indicator that changes color after sufficient scrubbing effort and time have been expended by a clinician to disinfect the medical device, giving positive visual feedback to the treating clinician. An external housing of the cap includes a disinfection medium, such as a disinfectant sponge that is coupled to a rotating collar. The housing is oriented so that the sponge contacts the medical device to be cleaned. Collar rotation in turn rotates the disinfectant sponge against the VAD, providing scrubbing action. A visualization chamber within the cap contains two isolated fluids of distinct colors. As the collar is rotated it mixes the two isolated fluids, changing color of the resultant mixture. When the visualization chamber shows the new, mixed third color, the medical device is disinfected.

17 Claims, 11 Drawing Sheets

49

70

MEDICAL DISINFECTION DEVICE WITH VISIBLE DISINFECTION INDICATOR

TECHNICAL FIELD

The present disclosure generally relates to a device for disinfecting and sterilizing medical devices, such as access ports. More particularly, the present disclosure generally relates to a disinfection device with a visual indicator that disinfection and sterilization of the medical device is completed.

BACKGROUND

Vascular access devices (VAD's) are commonly used therapeutic devices and include intravenous (IV) catheters. There are two general classifications of VAD's, peripheral catheters and central venous catheters. Bacteria and other microorganisms may gain entry into a patient's vascular system from access hubs, ports or valves upon connection to the VAD when delivering a fluid or pharmaceutical. Each access hub, port, valve or connection is associated with some risk of transmitting a catheter related bloodstream infection (CRBSI), which can be costly and potentially lethal.

In order to decrease CRBSI cases and to ensure VAD's are used and maintained correctly, standards of practice have been developed, which include disinfecting and cleaning procedures. Disinfection caps have been added to the Society for Healthcare Epidemiology of America (SHEA) guidelines and caps are also incorporated into the Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable. In particular, it has been found that health care providers may not completely understand the impact of not following scrubbing protocols. As a result, a health care provider may not disinfect the hub for the recommended amount of time.

SUMMARY

An aspect of the present disclosure pertains to a disinfection cap or device for disinfecting VADs and other medical devices, which gives positive visual feedback to the treating clinician whether disinfection is complete. The cap includes a visual indicator that changes color after sufficient scrubbing effort and time have been expended by a clinician to disinfect the VAD. An external housing of the cap includes a disinfection medium, such as a disinfectant sponge impregnated with a disinfectant or antimicrobial agent, which is coupled to a rotating collar. The external housing is oriented in a stationary position, so that the sponge contacts the VAD to be cleaned. Repetitive rotation of the collar rotates the disinfectant sponge against the VAD, providing scrubbing action. A visualization chamber of the cap contains two isolated fluids of distinct colors. As the collar is rotated it mixes the two isolated fluids, changing color of the resultant mixture to a third color, to indicate that the medical device being cleaned has been disinfected. When the visualization chamber shows the third, final mixed color, the clinician has scrubbed the VAD sufficiently to disinfect it, and can remove the now cleaned cap. The visualization chamber gives positive feedback to the treating clinician, eliminating uncertainty whether the cleaned device is properly disinfected.

In an exemplary embodiment of the present disclosure disinfection cap for medical devices, comprises an external housing, with a disinfection medium, such as a disinfectant sponge in the external housing. A rotatable collar is coupled to the disinfection medium, for rotating the medium. A visualization chamber is defined within and viewable outside the external housing. Respective first and second different colored fluids are retained in isolation from each other within the visualization chamber. A mixer within the visualization chamber is coupled to the collar, for mixing the first and second colored fluids upon rotation of the collar. Rotation of the collar rotates the disinfection medium against the medical device to be disinfected. Collar rotation also mixes the first and second colored fluids and changes them to a third color visible outside the external housing. The clinician receives visual feedback, via the color change, that disinfection of the medical device is completed. In some embodiments, the first and second colored fluids in the visualization chamber are isolated from each other by a membrane. Then, during collar rotation the mixer disrupts the membrane, allowing mixing of the previously isolated pair of colored fluids.

Another exemplary embodiment of the present disclosure is directed to a disinfection cap for medical devices, which includes an external housing having a proximal end and a disinfection cavity in an open distal end of that housing. An inner housing, within the disinfection cavity, is rotatable about a first rotation axis. The inner housing has an open distal end in communication with the open distal end of the external housing and a proximal end. A disinfection medium is oriented within the inner housing. A collar is rotatively coupled to the proximal end of the external housing about a second rotation axis that is coaxial with the first rotation axis. A shaft, oriented coaxially with the first and second rotation axes, is coupled to the proximal end of the inner housing and to the collar. The disinfection cap incorporates a visualization chamber, defined within the proximal end of the external housing and an interior surface of the collar. The visualization chamber is viewable outside the collar. First and second chambers are oriented within the visualization chamber, respectively containing respective first and second different colored fluids. A membrane is interposed between the first and second chambers and isolates them from each other. A mixer within the visualization chamber is coupled to the interior surface of the collar. The mixer disrupts the membrane upon rotation of the collar, causing the no longer isolated first and second colored fluids to mix with each other. Rotation of the collar scrubs the medical device being cleaned with the disinfection medium and also mixes the first and second colored fluids. As the first and second colored fluids are being mixed, they change to a third color, visible outside the external housing. When a clinician views the third color within the visualization chamber, he or she knows that the medical device that was being cleaned is now disinfected and that further rotation of the collar is no longer necessary.

An additional exemplary embodiment of the present disclosure is directed to a method for disinfecting a medical device, by contacting it with a disinfection medium retained within an external housing of a disinfection cap. The external housing is held in a stationary position, with the disinfection medium, such as a disinfecting sponge, remaining in contact with the medical device. The medical device is disinfected by rotating a collar that is coupled to the disinfection medium, so that the latter scrubs the medical device. The collar is rotatively coupled to the external housing. A visualization chamber defined within the external housing is viewed from outside the external housing. The visualization chamber retains therein respective first and second colored fluids that are isolated from each other. The second colored fluid is a color different than that of the first colored fluid. The first and second colored fluids are mixed together with a mixer within the visualization chamber that is coupled to the collar. As the collar rotates, the mixing first and second colored fluids to change to a third color different than the first and second colors as the disinfection medium also rotates against and scrubs the medical device. The treating clinician ceases collar rotation upon visualization of the third color, giving visual feedback that the medical device is now disinfected.

BRIEF DESCRIPTION OF THE DRAWINGS

Exemplary embodiments of the disclosure are further described in the following detailed description in conjunction with the accompanying drawings, in which.

To facilitate understanding, identical reference numerals have been used, where possible, to designate identical elements that are common to the figures. The figures are not drawn to scale.

DETAILED DESCRIPTION

Figure 1:
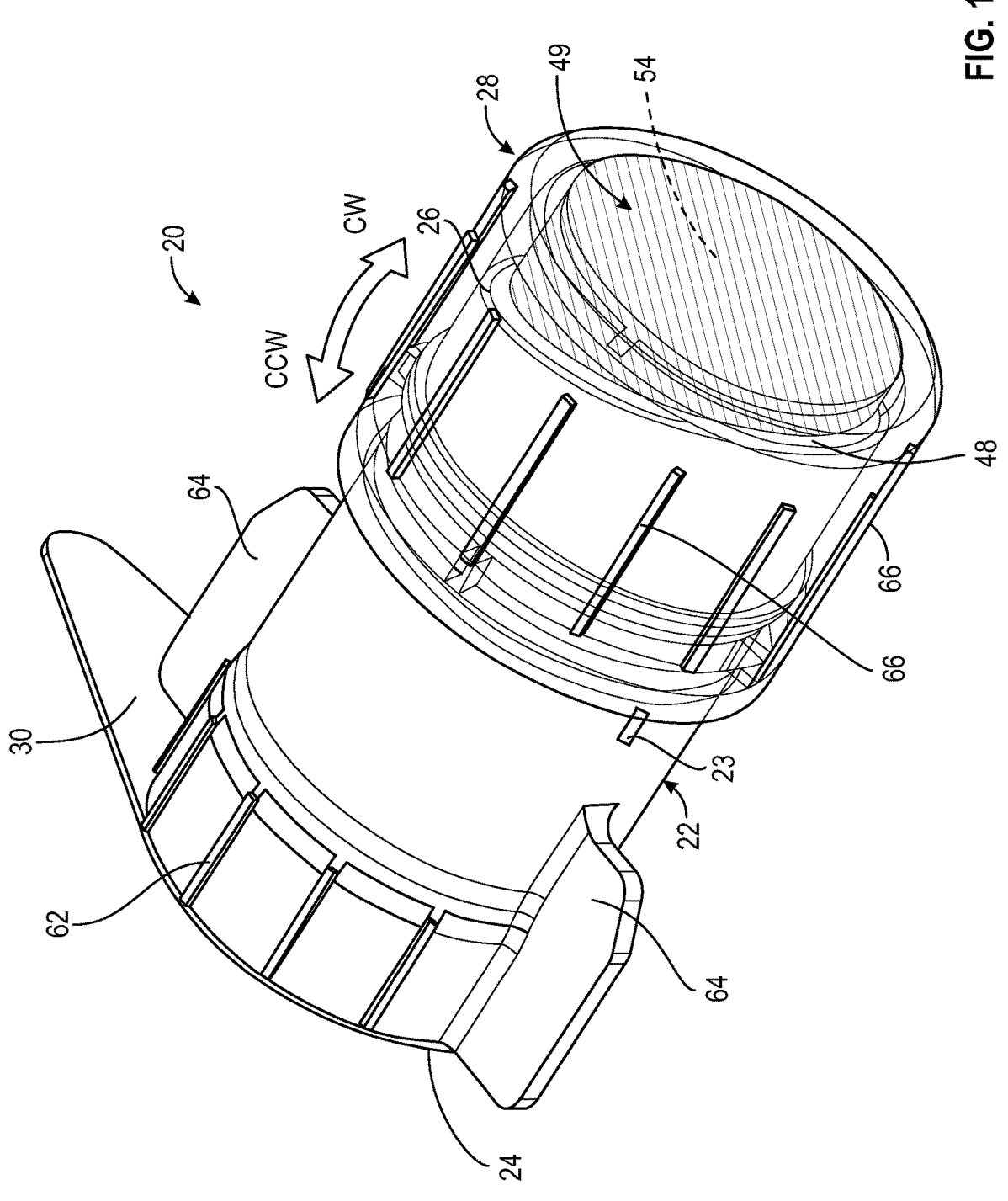
FIG. 1. is an isometric view of a disinfection cap of the present disclosure.

Before describing several exemplary embodiments of the disclosure, it is to be understood that the disclosure is not limited to the details of construction or process steps set forth in the following description. The disclosure is capable of other embodiments and of being practiced or being conducted in many ways.

Embodiments of the disclosure pertain to a disinfection cap or device for disinfecting medical connectors, such as vascular access devices (VAD's) or other medical devices. Various exemplary types of medical devices that are to be cleaned with a disinfection cap of the present disclosure are described below. The disinfection cap of the present disclosure includes a visual indicator that changes color after sufficient scrubbing effort and time have been expended by a clinician to disinfect the medical device, giving positive visual feedback to the treating clinician. An external housing of the cap includes a disinfection medium, such as a disinfectant sponge that is coupled to a rotating collar. The housing is oriented so that the sponge contacts the medical device to be cleaned. Collar rotation (e.g., by repetitive, sequential clockwise and counterclockwise rotation) in turn rotates the disinfectant sponge against the VAD, providing scrubbing action. A visualization chamber within the cap, viewable outside the cap, contains two isolated fluids of distinct colors. As the collar is rotated it mixes the two isolated fluids, changing color of the resultant mixture to a third color. When the visualization chamber shows the new third, mixed color, the medical device is disinfected.

In this disclosure, a convention is followed wherein the distal end of a device is the end closest to a patient, e.g., for delivery of one or more drugs to the patient, and the proximal end of the device is the end away from the patient and closest to a clinician or other medical practitioner. With respect to terms used in this disclosure, the following definitions are provided.

As used herein, the use of "a." "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar of a medical device (e.g., a VAD) that is the standard way of attaching syringes, catheters, hubbed needles, IV tubes and the like to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a vascular access device. (VAD). A Luer connector also has a distal end channel that releasably attaches the Luer connector to the hub of a VAD, and a proximal end channel that releasably attaches the Luer connector to the barrel of a syringe.

As used herein, ISO 80369-7:2016 defines a specification for standard Luer connectors including a 6% taper between the distal end and the proximal end. A male standard Luer connector increases from the open distal end to the proximal end. A female standard Luer connector decreases from the open proximal end to the distal end. According to ISO 80369-7:2016, a male standard Luer connector has an outer cross-sectional diameter measured 0.75 mm from the distal end of the tip of between 3.970 mm and 4.072 mm. The length of the male standard Luer taper is between 7.500 mm to 10.500 mm. The outer cross-sectional diameter measured 7.500 mm from the distal end of the tip is between 4.376 mm and 4.476 mm. As used herein, the phrases "male standard Luer connector" and "female standard Luer connector" shall refer to connectors having the dimensions described in ISO 80369-7, which is hereby incorporated by reference in its entirety.

As would be readily appreciated by skilled artisans in the relevant art, while descriptive terms such as "tip", "hub", "thread", "protrusion/insert", "tab", "slope", "wall", "top", "side", "bottom" and others are used throughout this specification to facilitate understanding, it is not intended to limit any components that can be used in combinations or individually or to require specific spatial orientations, to implement various aspects of the embodiments of the present disclosure.

According to still further exemplary implementations of the embodiments of the present disclosure, a needleless connector-type medical device to be cleaned may comprise female threads that are sized and have a thread pattern that will engage with a standard ISO594-2 type of male fitting and/or male threads that are sized and have a thread pattern that will engage with a standard ISO594-2 type of female fitting. An example of an ISO594-2 type of fitting is a Q-style fitting.

In one or more embodiments, a female connector-type medical device to be cleaned may be selected from the group consisting essentially of: needle-type connectors (for direct injection into a patient or insertion into a drug vial for aspiration of a drug dose therefrom), needle-free connectors, catheter Luer connectors, stopcocks, and hemodialysis connectors. In one or more embodiments, the needleless connector is selected from a Q-Syte™ connector, MaxPlus, MaxPlus Clear, MaxZero™, UltraSite®, Caresite®, In Vision-Plus®, Safeline®, OneLink, V-Link, ClearLink, NeutraClear™, Clave, MicroClave®, MicroClave® Clear, Clave Neutron, NanoClave®, Kendall™, Nexus, InVision-Plus®, Vadsite®, and Bionector®.

In one or more embodiments, the male connector-type medical device to be cleaned may be an intravenous tubing end or a stopcock.

Figure 2:
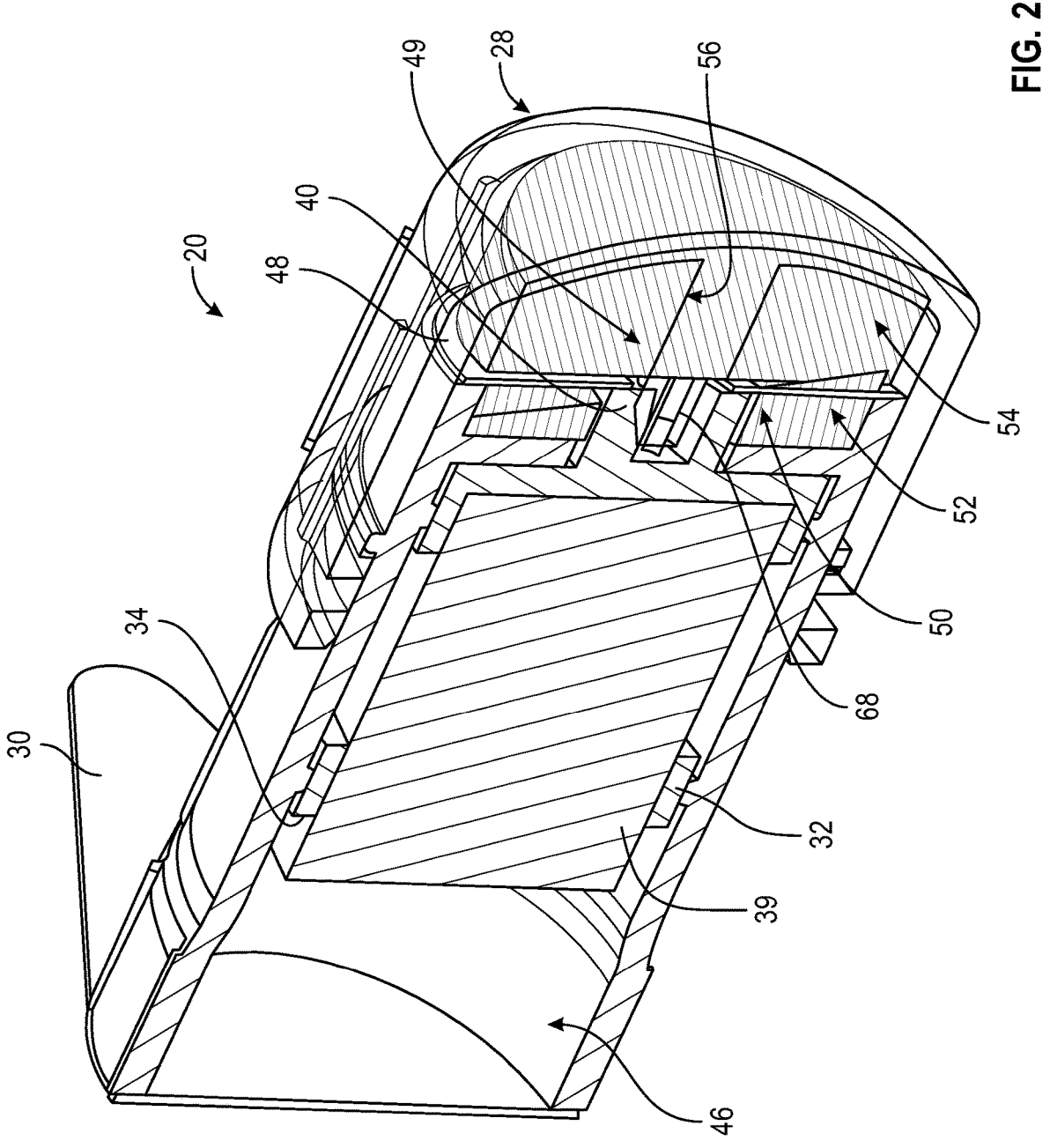
FIG. 2 is an axial cross-sectional view of the disinfection cap of FIG. 1.
Figure 3:
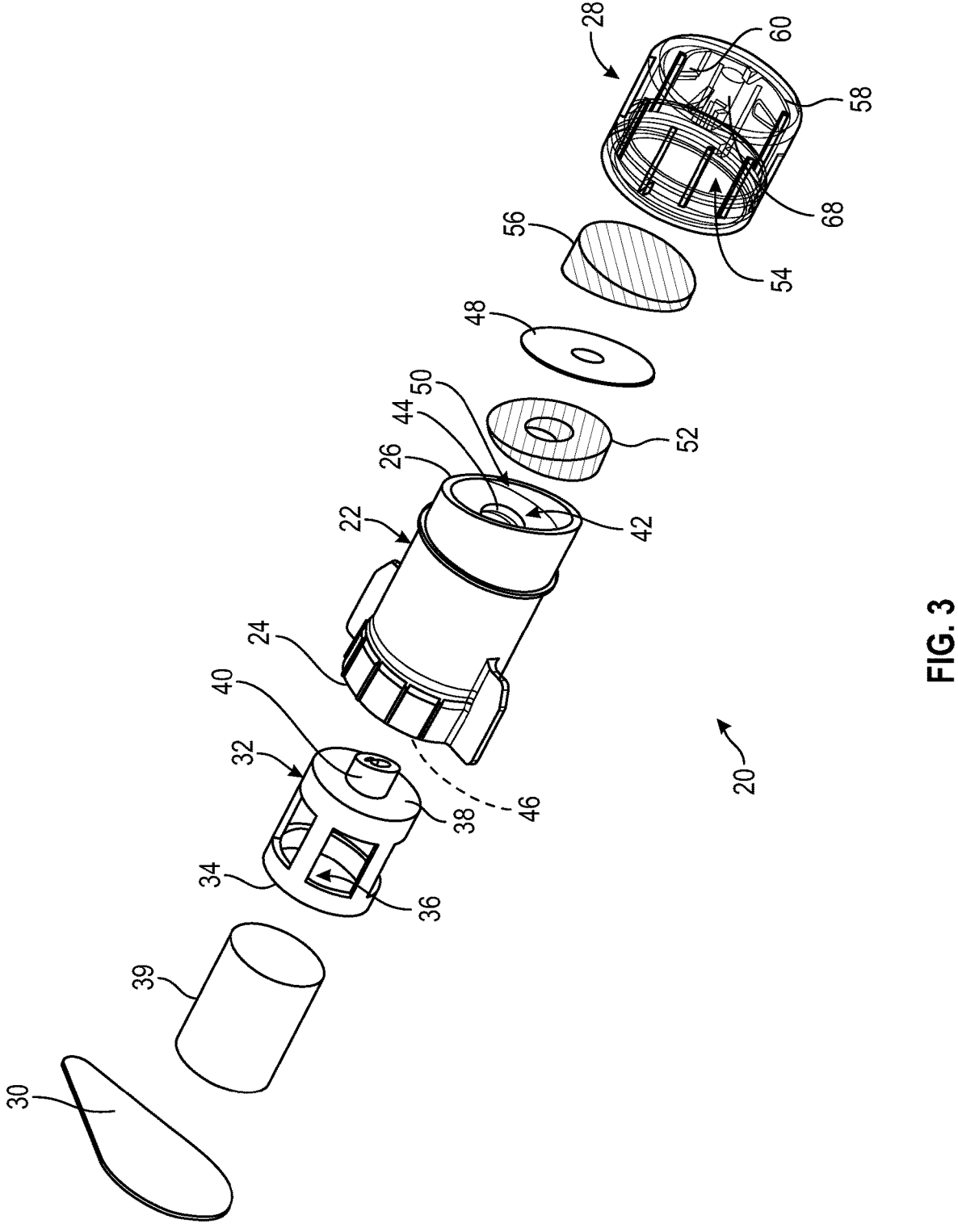
FIG. 3 is an exploded view of the disinfection cap of FIG. 1.

The following non-limiting examples demonstrate principles according to one or more embodiments of the disclosure. Referring now to the drawings, a first aspect of the present disclosure is shown in FIGS. 1-6, which illustrate its structural components and their interaction. The disinfection cap 20 of the present disclosure is also interchangeably referred to herein as a disinfection device or a cap. Referring specifically to FIGS. 1-3, the disinfection cap 20 includes an external housing 22, having an open distal end 24 and proximal end 26. A cup-shaped collar 28 is coupled to the proximal end 26 and is rotatable in both clockwise and counterclockwise directions (see arrows CW and CCW) about an axis that is coaxial with a centerline of the external housing 22. The open distal end 24 of the external housing 22 is sealed with a peelable tear tab 30 that is removable in the direction of the arrow P, the peelable tear tab, isolating the disinfection cap from the surrounding (ambient) environment until it is removed.

The disinfection cap 20 incorporates an inner housing 32, oriented within a disinfection cavity 46 of the external housing 22. The inner housing 32 is rotatable in both clockwise and counterclockwise directions (sec arrows CW and CCW) about an axis that is coaxial with a centerline of the external housing 22 and the rotational axis of the collar 28. The inner housing 32 has an open distal end 34 that is communication with an inner housing cavity 36 and a proximal end 38. The inner housing cavity contains a disinfection medium, such as a disinfectant sponge 39, which is infiltrated with a disinfectant or antimicrobial agent. A shaft 40 (also referred to as a mounting stud) couples the proximal end 38 of the inner housing 32 and the collar 28, so that rotation of the collar also rotates the inner housing. The shaft 40 is oriented coaxial with the rotational axes of the collar 28, the inner housing 32 and the centerline of the external housing 22. The shaft 40 extends axially toward the collar 28, passing through an open-ended fluid cavity 42 and a through-bore 44, formed in the proximal end 26 of the external housing 22.

A membrane-like tear seal 48 (also referred herein as a membrane) circumscribes the shaft 40 and is sealed along the axial peripheral edge of the fluid cavity 42. The tear seal is constructed from a hydrophobic plastic material. The tear seal 48 is oriented at an acute angle relative to the centerline of the external housing 22 as well as the common, coaxial rotational axes of the collar 28 and the inner housing 32.

Figure 6:
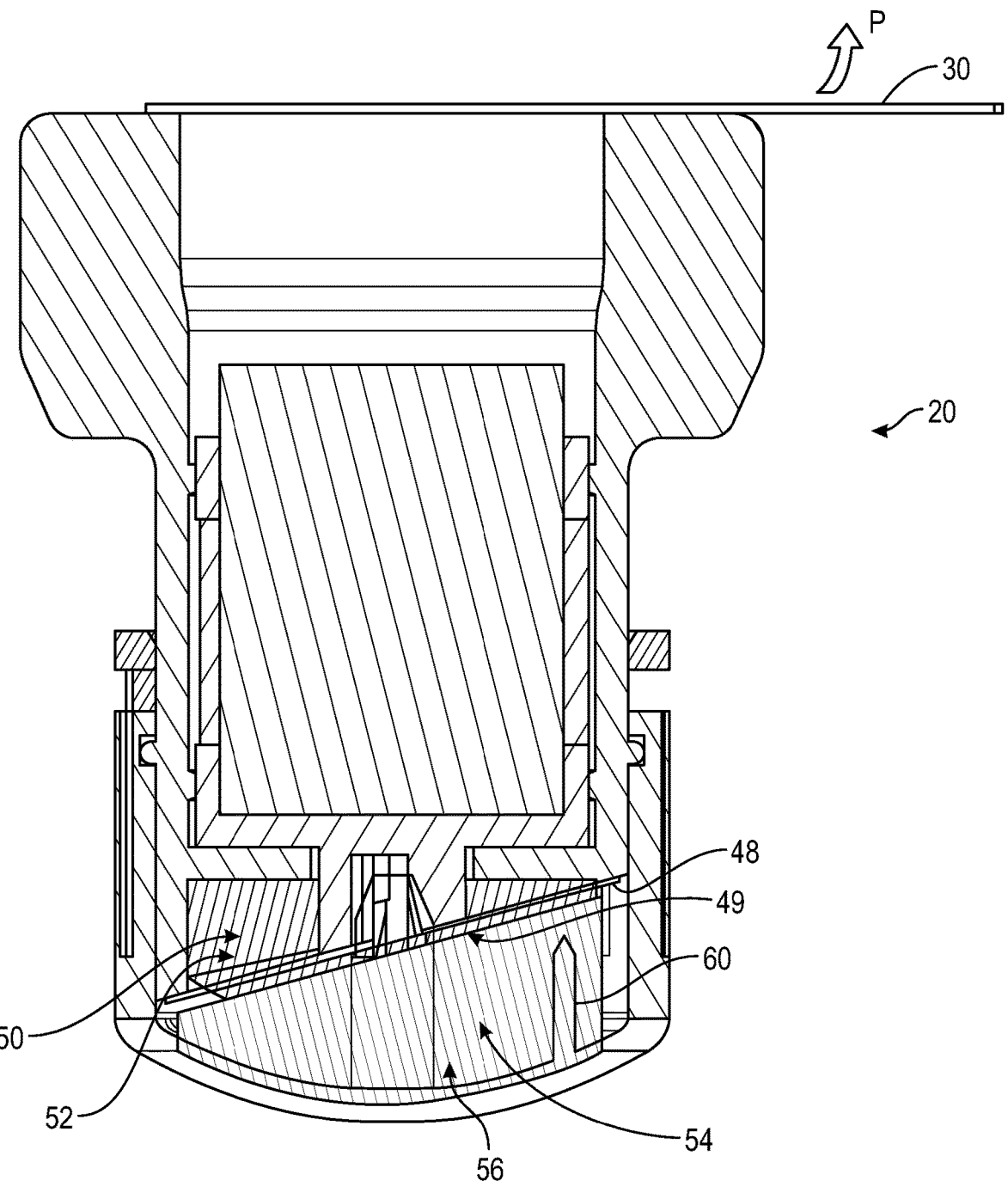
FIG. 6. is an axial cross-sectional view of the disinfection cap of FIG. 5, showing isolated first and second fluids in the visualization chamber, separated by a membrane.

Referring specifically to FIGS. 2, 3, and 6, the disinfection cap 20 forms a visualization chamber 49 within the fluid cavity 42 at the proximal end 26 of the external housing 22 and the interior of the cup-shaped collar 28. In some embodiments, the collar 28 is constructed of clear or transparent material, so that the visualization chamber 49 is visible outside the disinfection cap 20 and its external housing 22. In other embodiments, the collar is constructed with a clear or transparent window for viewing the visualization chamber. The visualization chamber 49 comprises a first chamber 50 that is oriented within the fluid cavity 42 on a distal side of the tear seal 48, and a second chamber 54 on a proximal side of the tear seal, within the interior of the cup-shaped collar 28. The first chamber 50 contains a first colored fluid 52 (e.g., red) and the second chamber 54 contains a second colored fluid 56, different from the first colored fluid (e.g., blue). Thus, the first colored fluid 52 is isolated from the second colored fluid 56 by the membrane-like tear seal 48.

Figure 4:
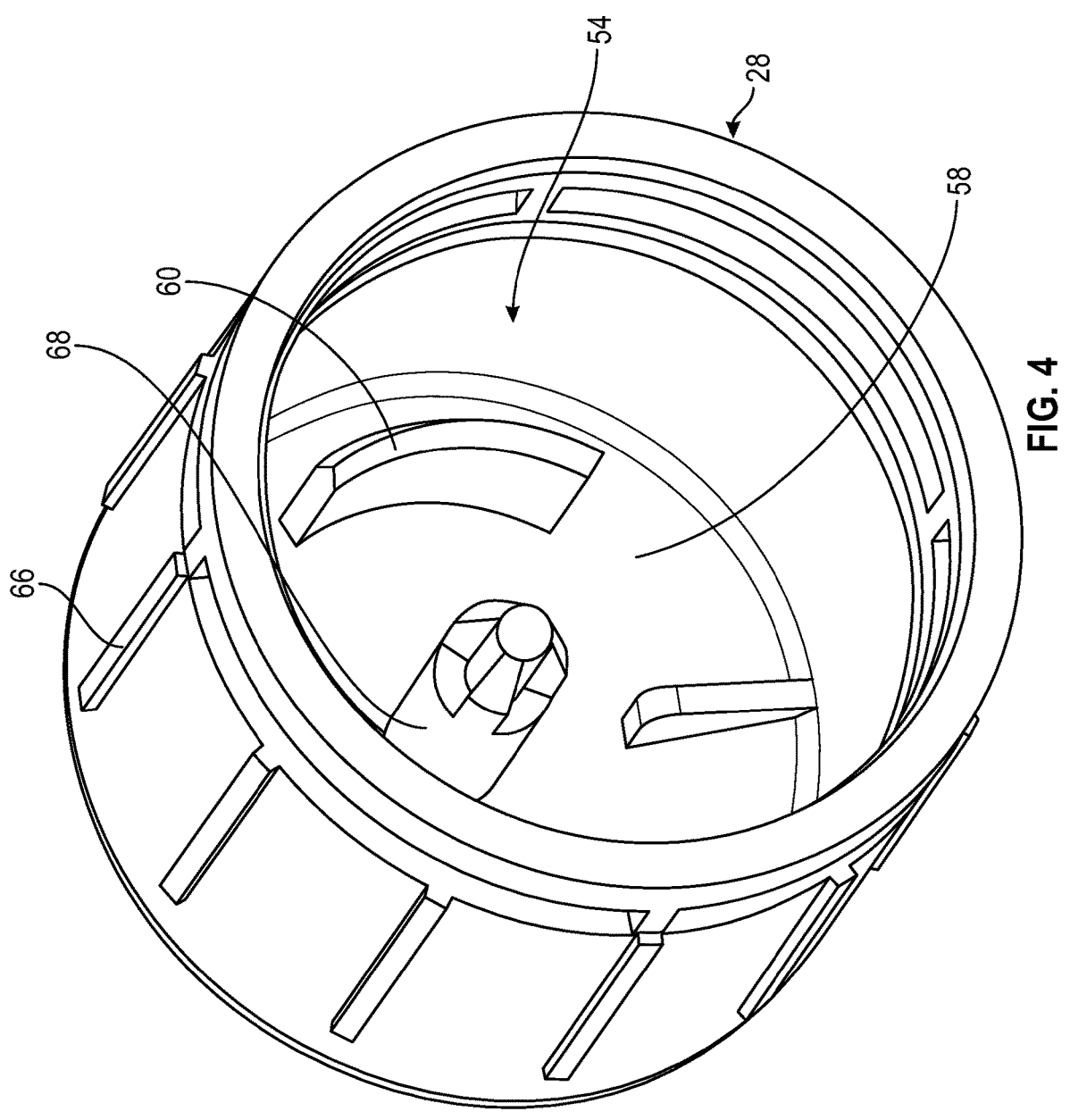
FIG. 4 is an isometric view of the collar of the disinfection cap of FIG. 1.
Figure 5:
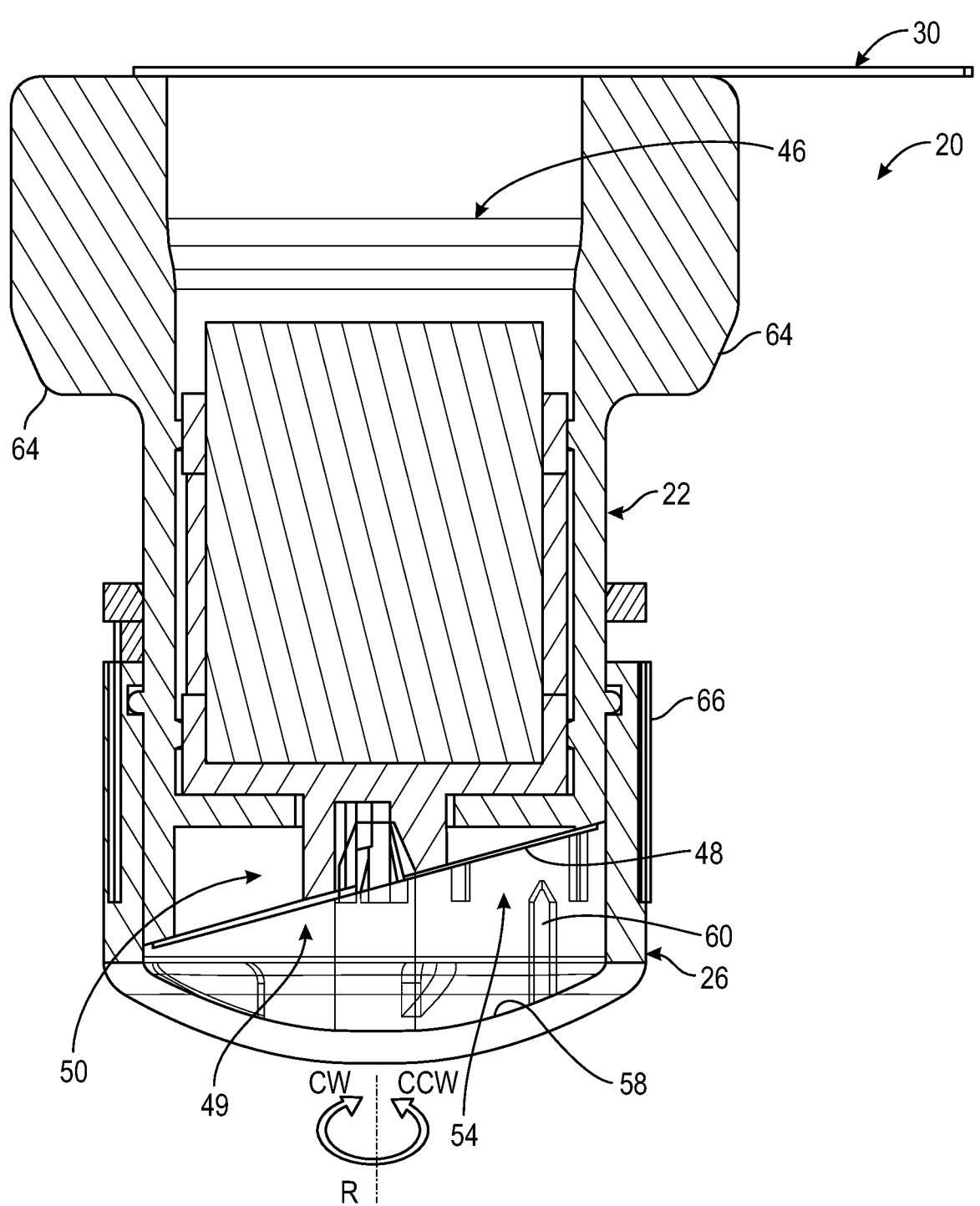
FIG. 5 is an axial cross-sectional view of the disinfection cap of FIG. 1, with an empty visualization chamber, showing the collar in a first rotational position.

Referring to FIGS. 4 and 5, an inner wall surface 58 of the cup-shaped collar 28 includes a mixer or cutter 60 that projects axially toward the fluid cavity 42, within the visualization chamber 49. In a new, not yet used, disinfection cap 20, the cutter 60 is positioned within the second chamber 54 out of contact with the membrane-like tear seal 48. The inner wall surface 58 of the collar 28 also incorporates a collar mounting stud 68 that is coupled to the mounting shaft 40, so that rotation of the collar rotates simultaneously the inner housing 32 with its affixed disinfectant sponge 39, and the cutter 60 relative to the tear seal 48.

FIGS. 5-8 show interaction of the rotating mixer/cutter 60 with the membrane-like tear seal 48, and how that interaction causes visual color change within the visualization chamber 49. FIG. 5 illustrates the visualization chamber 49 without any colored fluids in the first chamber 50 and the second chamber 54, which are isolated from each other by the intact tear seal 48. In FIG. 6 the isolated first chamber 50 and second chamber 54 are filled respectively with the first colored fluid 52 (e.g., red) and the second colored fluid 56 (e.g., blue). As the intact tear seal 48 is maintaining isolation of the colored fluids, only the second colored fluid 56 is visible through the proximal axial end of the collar 28. In the color examples of FIG. 6, a clinician viewing the transparent or translucent collar 28 sees only a blue-colored visualization chamber 49.

Figure 7:
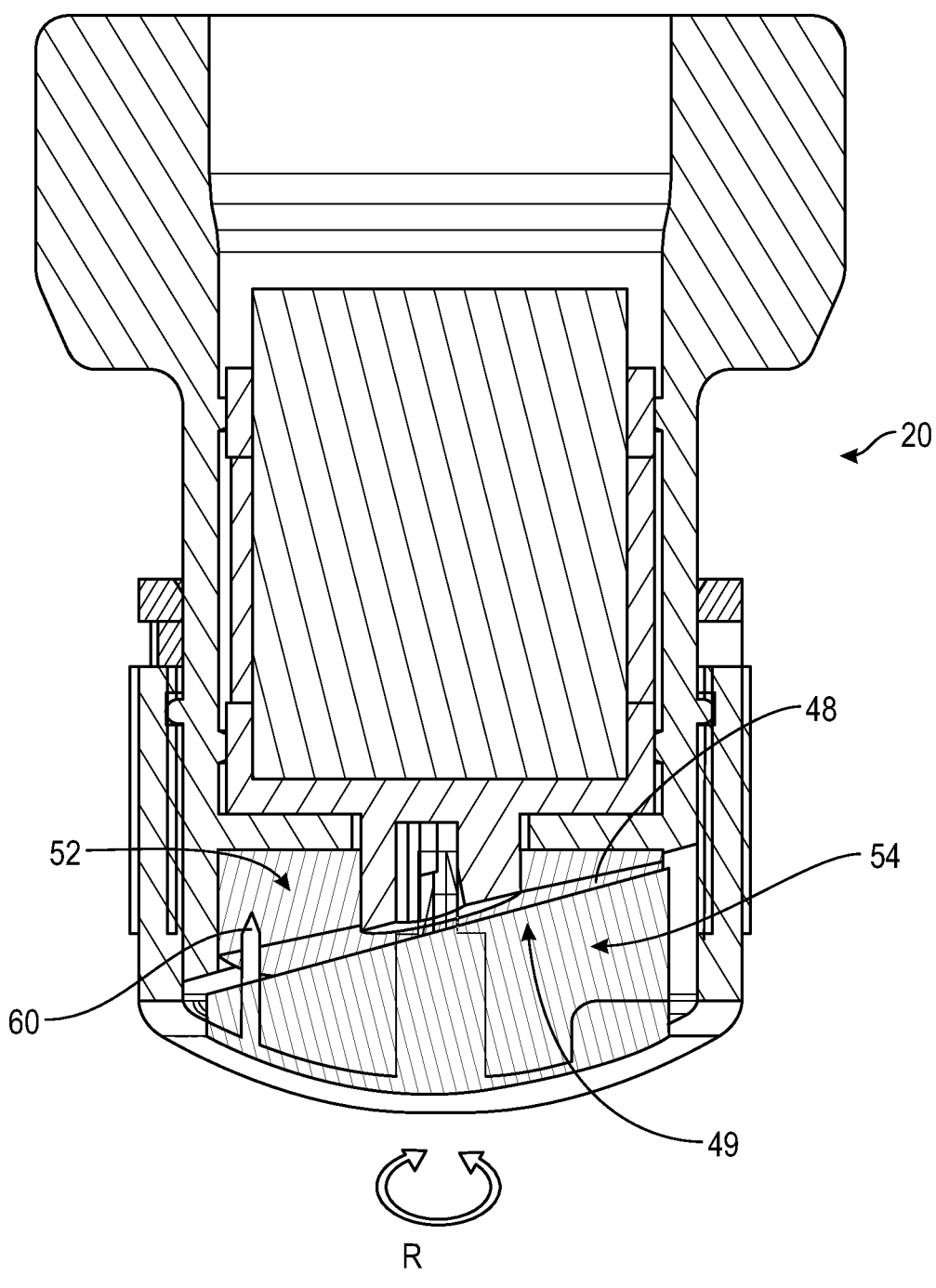
FIG. 7 is an axial cross-sectional view of the disinfection cap of FIG. 6, showing the collar in a second rotational position, disruption of the membrane, and partial mixing of the first and second fluids.

Referring now to FIG. 7, as the clinician rotates the collar 28 while maintaining the remainder of the disinfection cap 20 stationary, arcuate cutting motion of the mixer/cutter 60 cuts or otherwise disrupts structural integrity of the membrane-like tear seal 48, allowing mixing of the first 52 and second 56 colored fluids. Repetitive clockwise and counterclockwise rotation of the collar 28, as shown by the bidirectional arrow R, continues mixing and homogenization of the first 52 and second 56 color fluids.

Figure 8:
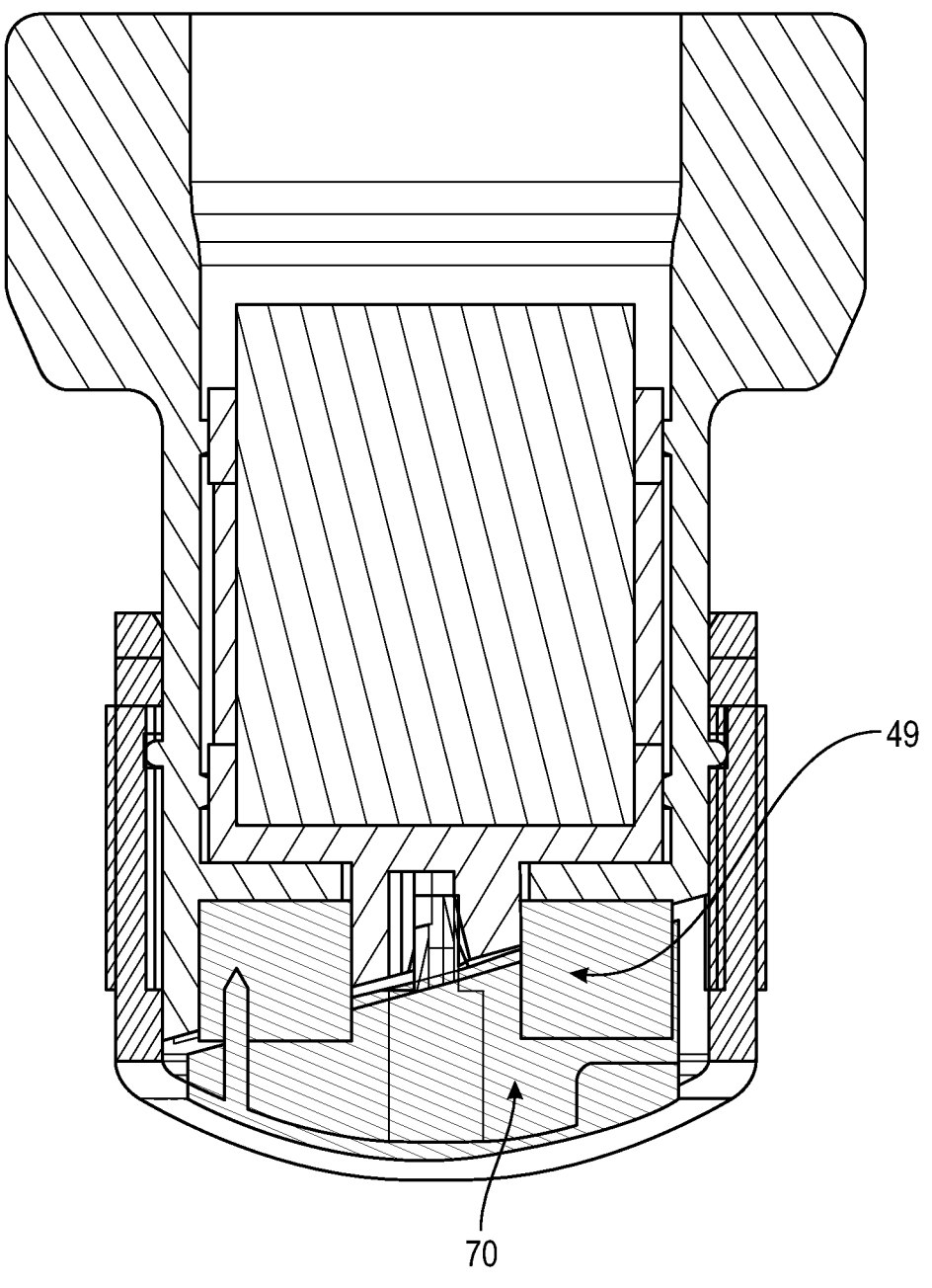
FIG. 8 is an axial cross-sectional view of the disinfection cap of FIG. 7, showing complete mixing of the first and second fluids and their resultant color change.

Referring now to FIG. 8, after repetitive rotation of the collar 28, the homogenized fluids change to a third color fluid, a mixed secondary color 70. Using the example of red-colored first colored fluid 52 and blue-colored second colored fluid 56, their mixture results in purple-colored fluid as the mixed secondary color 70, as viewed in FIG. 8. In other embodiments, different pairs of first and second fluid primary colors are chosen; when mixed they change to other secondary colors. For example, in another embodiment the pair of primary colors chosen for each respective first 50 and second 54 chambers in the visualization chamber 49 are yellow and blue, which mix to secondary color green. In other embodiments the primary color pair is red and yellow, which mix to secondary color orange. In an aspect of the present disclosure, different primary color pair/secondary color combinations are chosen for the visualization chamber 49 for different disinfection scrubbing times of the disinfectant sponge 39. For example, one color combination is used for ten-second disinfection cycle, another for a 30-second disinfection cycle.

The time and number of rotation cycles needed to homogenize the first 52 and second 56 fluids sufficiently to change them to the third color, a mixed secondary color 70 varies by the chosen fluid composition, density, and viscosity. Homogenization time and number of rotation cycles needed to cause the fluid color change to the mixed secondary color 70 corresponds to the chosen time and scrubbing effort necessary for the simultaneously rotating disinfectant sponge 39 to disinfect medical devices. In accordance with an aspect of the present disclosure, the number of rotations of the collar 28 needed to homogenize the first 52 and second 56 colored fluids corresponds to an amount of scrubbing action by the disinfectant sponge 39 needed to disinfect a portion of a medical device. Thus, the visualization chamber 49 of the disinfection cap 20 provides passive visual indication to the medical clinician user that the disinfection of the medical device to be cleaned is completed.

When using the disinfection cap 20, the external housing 22 is held in a stationary position during relative rotation of the coupled inner housing 33/sponge 39 and the collar 28. To assist stationary positioning of the external housing 22, it incorporates housing grasping ribs 62 and housing grasping wings 64 to facilitate slip-free, one-handed retention of the disinfection cap 20 by a treating clinician. Similarly, the collar 28 includes collar grasping ribs 66 to facilitate its rotation with the clinician's other hand. For example, the treating clinician holds the external housing 22 in a stationary position by holding the housing grasping ribs 62 and/or the grasping wings 64 and selectively rotates the collar 28 by grasping the collar grasping ribs 66. In one or more embodiments, the external housing 22 and/or the collar 28 includes additional grip enhancement features, such as a textured surface.

Having described generally the structural components of the disinfection cap 20 and the interaction of those components, as shown in FIGS. 1-5, a more detailed description of various embodiments of individual components follows. The more detailed description of specific components is exemplary in nature and is not intended to limit overall description and understanding of this disclosure.

In one or more embodiments, the tear tab 30 is a peelable seal, which comprises an aluminum or multi-layer polymer film peel back top. The tear tab 30 seal minimizes entry of potential particulate hazard and also provides a substantially impermeable enclosure for the external housing 22, provides a leak prevention and protection enclosure, protects the absorbed, infiltrated contents of the disinfectant sponge 39 or other disinfectant media contained within the disinfection cavity 46, and/or maintains a sealed, sterilized environment. The tear tab 30 seal provides a sufficient seal at a range of temperatures, pressures, and humidity levels expected within a medical treatment facility. In one or more embodiments, the tear tab 30 seal comprises an aluminum or multi-layer polymer film peel back top. In some embodiments, the tear tab 30 seal is heat-sealed or induction-sealed to the distal end 24 of the external housing 22.

The disinfectant sponge 39 or other alternative absorbent material retained within the inner housing 32 includes an absorbed or infiltrated, liquid or gel, disinfectant or an antimicrobial agent for disinfecting medical device that is to be cleaned with the disinfection cap 20. In one or more embodiments, the absorbent material is a nonwoven material, foam, or a sponge having a porous structure. In a specific embodiment, the foam is a polyurethane foam. In a specific embodiment, the absorbent material is a sponge.

The disinfectant sponge 39 retains disinfectant or antimicrobial agent, which may be in fluid form, in its porous structure due to surface tension and releases disinfectant or antimicrobial agent when squeezed or compressed by contact with a medical device that is to be cleaned by the disinfection cap 20. The disinfection cap 20 is compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethyl paraben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel. In one or more specific embodiments, the disinfectant or antimicrobial agent is 70% isopropyl alcohol (IPA).

In an aspect of the present disclosure, density of the first 52 and second 56 colored fluids and their mixing properties to change to the third color, the mixed secondary color 70 are selected to determine both the mixing time and the corresponding time of disinfection by the disinfectant medium/sponge 39. Density and other chemical properties of the colored fluids 52 and 56 are adjusted as needed to achieve the desired disinfection scrubbing time of the disinfection cap 20. In an aspect of the disclosure glycerol fluid is utilized as the mixing fluid in the visualization chamber 49, due to its higher density and miscible nature. Glycerol also possesses antimicrobial and antiviral properties. Glycerol is widely used in medical, pharmaceutical and personal care products. Glycerol is easily miscible with water and alcohol, and mixes well with color dyes. It has a relatively high density of approximately 1.26 g/cc, is inexpensive, biodegradable, nontoxic and non-irritating to the human digestive system, skin and mucous membranes.

Components of the disinfection cap 20 are constructed from any of a number of types of medical grade, plastic materials such as polycarbonate, polypropylene, polyethylene, glycol-modified polyethylene terephthalate, acrylonitrile butadiene styrene or any other moldable plastic material used in medical devices. In one or more embodiments, the disinfection cap 20 comprises a polypropylene or polyethylene material.

Figure 9:
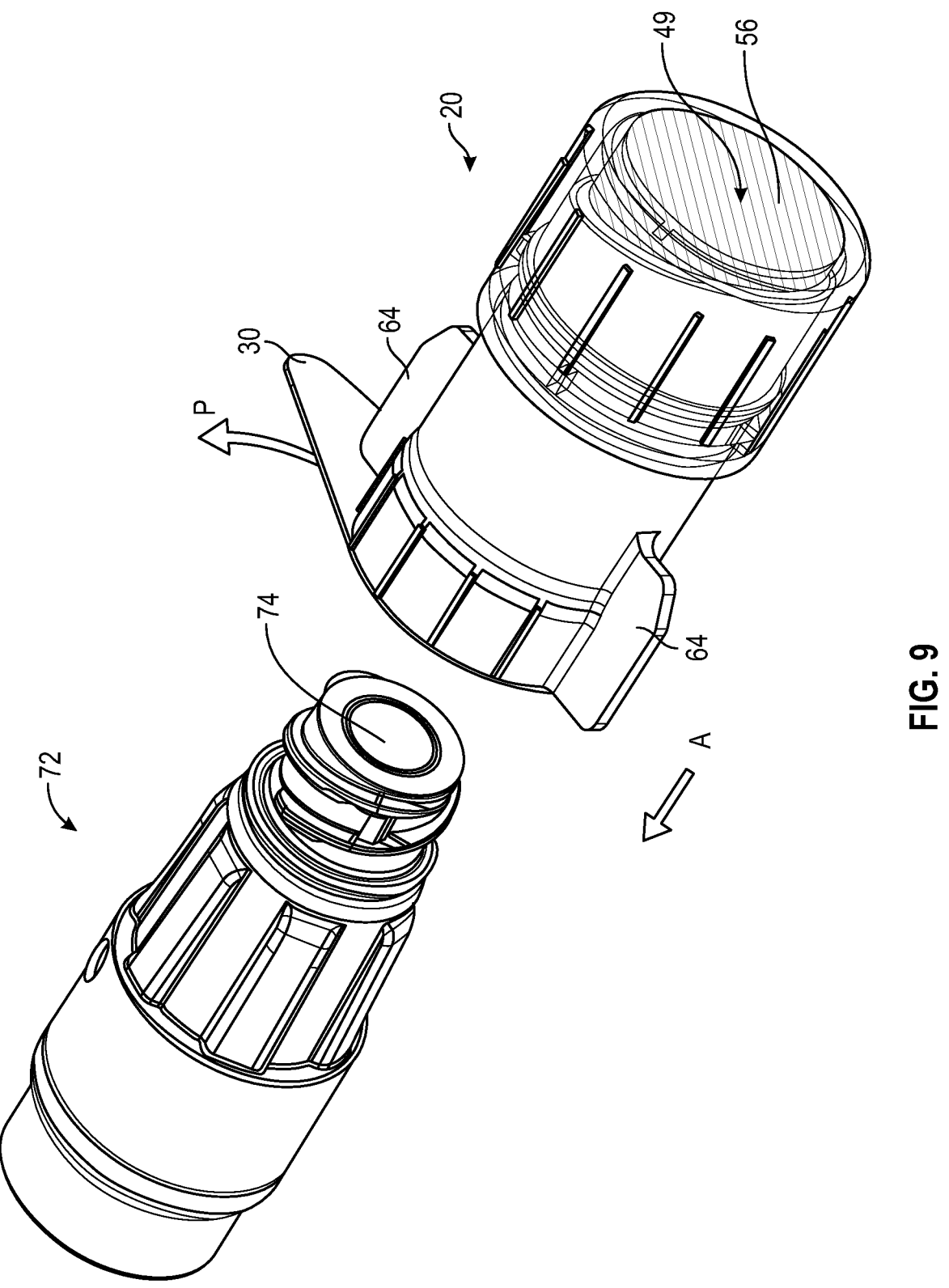
FIG. 9 is an isometric view of the disinfection cap of FIG. 1, prior to cleaning of a catheter port-type medical device.

Referring to FIGS. 3 and 9-11, aspects of the present disclosure are directed to methods for disinfecting surfaces of medical devices, such as a needle free connector (NFC), any other type of needleless connector, catheter Luer connector, stopcock, hemodialysis connector, and other types of vascular access devices (VAD's), including, but not limited to peripheral catheters and central venous catheters. For purposes of illustration of the methods, in FIG. 9 an exemplary disinfection cap 20 of the present disclosure will now be described when used to disinfect a catheter port 72, which includes a hub portion having a substantially frustoconical- or cylindrical-shaped outer hub surface that is axially symmetrical about a central axis. The hub portion of the catheter port 72 further includes an access surface that includes a septum 74. The access surface and septum 74 are oriented substantially transverse to central axis of the catheter port 72. In FIG. 9 the centerline axis of the disinfection cap 20 is coaxially aligned, in spaced relationship with that of the catheter port 72.

Figure 10:
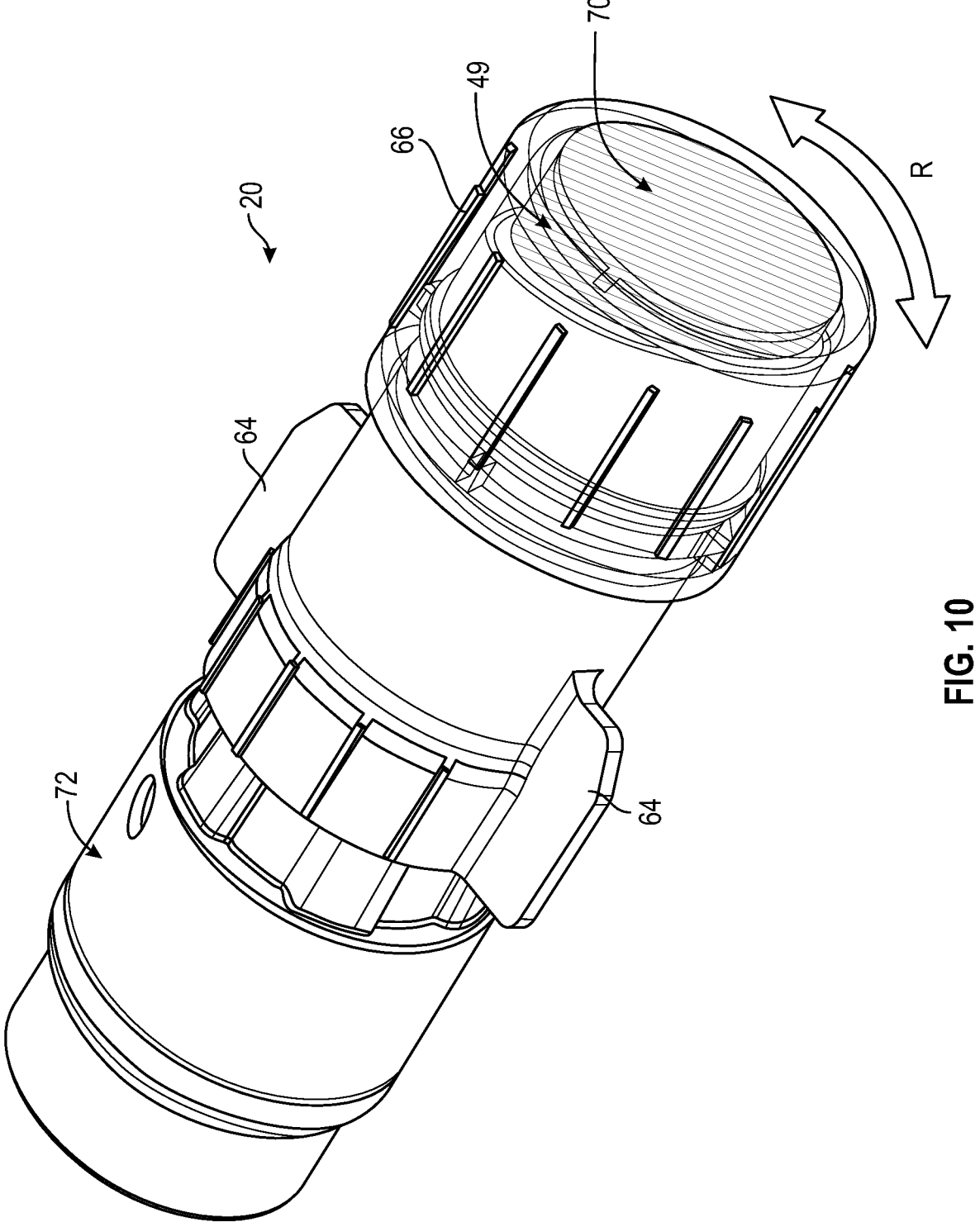
FIG. 10 is an isometric view of the disinfection cap of FIG. 9 after cleaning the catheter port-type medical device, prior to removal of the cap.
Figure 11:
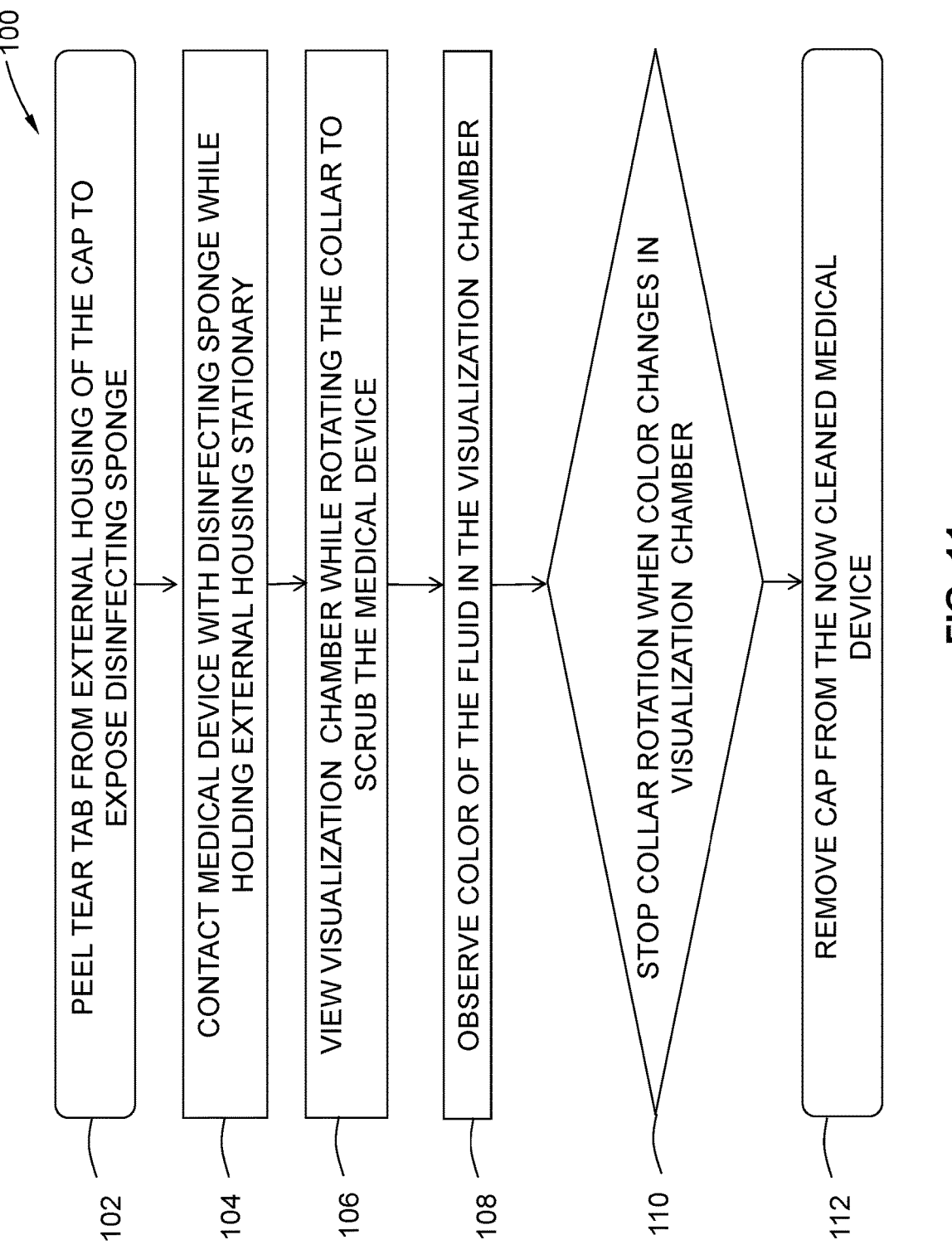
FIG. 11 is a flowchart depicting a method for disinfecting a medical device with a disinfection cap of the present disclosure.

Referring to FIGS. 3 and 9 and the flow chart 100 of FIG. 11, in step 102 the treating medical clinician who will disinfect the catheter port 72 and its septum 74 peels the tear tab 30 away from the distal end 24 of the external housing 22 of the disinfection cap 20, as shown by the arrow P. The intact tear tab 30 indicates that the disinfection cap 20 has not been previously used to clean a medical device. Viewing the visualization chamber 49 through the rotatable collar 28 comprising translucent or clear material, the initial visible color of the second colored fluid 56 is the primary color blue. This means that the second colored fluid 56 remains isolated from the first colored fluid 52 in the visualization chamber 49. In addition to the intact tear tab 30, the blue color of the second colored fluid 56 indicates to the clinician that the disinfection cap 20 has not been used previously to clean a medical device. In FIG. 10, in accordance with step 104 of the flow chart 100, the clinician utilizes the grasping ribs 62 and/or the grasping wings 64 of the external housing 22 to advance the axially aligned disinfection cavity 46 of the disinfection cap 20 over the catheter port 72-type medical device until the disinfection sponge 39 contacts and presses against the septum 74. The clinician holds the external housing 22 of the disinfection cap 20 in a stationary position relative to the catheter port 72, such as by grasping the housing grasping ribs 62 and/or the grasping wings 64. In accordance with an aspect of the present disclosure, compression of the disinfection sponge 39 releases the disinfectant or antimicrobial agent from the sponge or other absorbent material such that the disinfectant or antimicrobial agent contacts the septum 74 and surrounding surfaces of the port 72

As previously described, rotation of the collar 28 of the disinfection cap 20, as shown by the double arrow R in FIG. 10 and step 106 of the flow chart 100, causes corresponding rotation of the inner housing 32, by virtue of their mechanical coupling through shaft 40, and thus rotation of the disinfectant sponge 39. In accordance with an aspect of the present disclosure, in steps 106 and 108 the collar 28 is rotated sequentially and repeatedly clockwise and counterclockwise by the treating clinician grasping the collar grasping ribs 66, while observing color of the fluid in the visualization chamber 49. Rotation of the collar 28 frictionally engages the disinfectant sponge 39 against the septum 74 and related surfaces to provide a scrubbing action that actively disinfects them. The twisting, rotational motion of the disinfecting sponge 39 increases disinfection activity when compared to use of 70% isopropyl alcohol (IPA) impregnated pads alone. In one or more embodiments, active disinfection due to rotation of the collar 28 is in addition to the passive chemical disinfection of the septum 74 and related surfaces due to contact between the liquid or gel disinfectant or antimicrobial agent expressed by the disinfectant sponge 39. An advantage of using the disinfection cap 20 of the present disclosure is that it disinfects medical devices with both chemical disinfectant expressed by the disinfectant sponge 39 (passive disinfection) and scrubbing action by the sponge (active mechanical disinfection). Thus, the combination of passive disinfection with active disinfection results in improved disinfection results. This scrubbing step of the medical device can be performed for around 10-15 seconds to achieve a minimum log reduction of microbes (>4 log). In aspects of the present disclosure, the visualization chamber 49 changes color after a desired amount of disinfectant scrubbing was performed (e.g., a specific quantity of mechanical mixing by collar 28 rotational scrubbing and number of seconds of scrubbing activity).

As previously described, rotation of the collar 28 simultaneously causes the mixer/cutter 60 within the visualization chamber 49 to disrupt the tear seal 48, thereby mixing the first 52 and second 56 colored fluids together, causing the mixed first and second colored fluids to change to the third color being a mixed secondary color 70 that is different than the first and second colors.

Referring to step 110 of the flowchart 100, the clinician stops collar 28 rotation when visible color in the visualization chamber 49 changes from the initial primary color of the second colored fluid 56 to the mixed secondary color 70. In accordance with an aspect of the present disclosure, the number of rotations of the collar 28 needed to change the visible color in the visualization chamber 49 from the initial primary color of the second colored fluid 56 to the mixed secondary color 70 corresponds to an amount of scrubbing action and scrubbing time needed to disinfect the septum 74 and its related surfaces. Thus, the visualization chamber 49 of the disinfection cap 20 device provides passive visual indication to the treating clinician that the disinfection of the septum 74 is completed. At step 112 of the flowchart 100, the clinician removes the disinfection cap 20 from the now cleaned catheter port 72 after observation in step 110 that the mixed secondary color 70 is visible in the visualization chamber 49.

In some embodiments, the disinfection cap 20 further includes a tamper evident structure 23 that indicates whether or not the collar 28 has already been rotated. The tamper evident structure 23 according to some embodiments comprises a sticker or a peel off label or tear away label.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A disinfection cap for medical devices, comprising:
an external housing having an open distal end;
a disinfection medium in the external housing, in communication with the open distal end of the external housing;
a rotatable collar coupled to the disinfection medium;
a visualization chamber at least partially defined within and viewable outside the external housing;
respective first and second different colored fluids respectively having a first color and a second color retained in isolation from each other within the visualization chamber; and
a mixer within the visualization chamber, coupled to the rotatable collar, for mixing the respective first and second different colored fluids upon rotation of the rotatable collar, wherein rotation of the rotatable collar mixes the respective first and second different colored fluids and changes them to a third color visible outside the external housing.

2. The disinfection cap of claim 1, further comprising:
first and second chambers within the visualization chamber, respectively containing the first and second colored fluids;
a membrane interposed between and isolating the first and second chambers from each other; and
the mixer disrupting the membrane upon rotation of the rotatable collar and causing the respective first and second different colored fluids to mix with each other.

3. The disinfection cap of claim 2, the mixer comprising a cutter for disrupting the membrane.

4. The disinfection cap of claim 3, the cutter coupled to an interior surface of the rotatable collar, with said interior surface of the rotatable collar forming at least part of the visualization chamber.

5. The disinfection cap of claim 4, at least a portion of the rotatable collar comprising translucent or clear material for external viewing of fluid colors within the visualization chamber.

6. The disinfection cap of claim 1, further comprising:
the external housing having a disinfection cavity in the open distal end thereof and a proximal end;
the disinfection medium oriented within the disinfection cavity
the rotatable collar rotatively coupled to the proximal end of the external housing and coupled to the disinfection medium by a shaft; and
the visualization chamber defined within the proximal end of the external housing and an interior surface of the rotatable collar, and viewable outside the rotatable collar.

7. The disinfection cap of claim 6, further comprising the visualization chamber defining therein a first chamber retaining the first colored fluid and a second chamber retaining the second colored fluid, separated by a membrane within the visualization chamber, the mixer disrupting the membrane upon rotation of the rotatable collar and causing the respective first and second different colored fluids to mix with each other and change to the third color.

8. The disinfection cap of claim 7, further comprising the membrane oriented at an acute angle within the visualization chamber relative to a rotational axis of the rotatable collar.

9. The disinfection cap of claim 7, the first colored fluid comprising glycerol and a first color dye, and the second colored fluid comprising glycerol and a second color dye.

10. The disinfection cap of claim 6, further comprising:
an inner housing disposed within the disinfection cavity and retaining the disinfection medium; and
a shaft coupled to the inner housing and the rotatable collar, for rotating the inner housing.

11. The disinfection cap of claim 10, further comprising the shaft passing through the visualization chamber.

12. The disinfection cap of claim 10, the disinfection medium comprising a disinfectant sponge having a disinfection agent retained therein.

13. The disinfection cap of claim 6, further comprising a peelable tear tab covering the open distal end of the external housing to isolate the disinfection cavity from an ambient environment.

14. A disinfection cap for medical devices, comprising:
an external housing having a proximal end and a disinfection cavity in an open distal end thereof;
an inner housing within the disinfection cavity, rotatable about a first rotation axis, the inner housing having an open distal end in communication with the open distal end of the external housing and a proximal end; and
a disinfection medium within the inner housing
a collar rotatively coupled to the proximal end of the external housing about a second rotation axis that is coaxial with the first rotation axis;
a shaft, coaxial with the first and second rotation axes, coupled to the proximal end of the inner housing and the collar;
a visualization chamber defined within the proximal end of the external housing and an interior surface of the collar, and viewable outside the collar;

first and second chambers within the visualization chamber, respectively containing respective first and second different colored fluids;

a membrane interposed between and isolating the first and second chambers from each other; and a mixer within the visualization chamber, coupled to the interior surface of the collar, the mixer disrupting the membrane upon rotation of the collar and causing the respective first and second different colored fluids to mix with each other, wherein rotation of the collar mixes the respective first and second different colored fluids and changes them to a third color visible outside the external housing.

15. The disinfection cap of claim 14, the disinfection medium comprising a disinfectant sponge.

16. The disinfection cap of claim 15, wherein the disinfectant sponge incorporates a disinfectant or antimicrobial agent that is selected from a group consisting essentially of isopropyl alcohol, ethanol, 2-propanol, butanol, methylparaben, ethyl paraben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

17. The disinfection cap of claim 16, wherein the disinfectant or antimicrobial agent comprises at least one of chlorhexidine gluconate and chlorhexidine diacetate.

\* \* \* \* \*